United States Patent
Blohm et al.

(10) Patent No.: US 10,261,041 B2
(45) Date of Patent: Apr. 16, 2019

(54) INTEGRATED DISPOSABLE CHIP CARTRIDGE SYSTEM FOR MOBILE MULTIPARAMETER ANALYSES OF CHEMICAL AND/OR BIOLOGICAL SUBSTANCES

(71) Applicant: Fraunhofer-Gesellschaft zur Foerderung der angewandten Forschung e.V., Munich (DE)

(72) Inventors: Lars Blohm, Heide (DE); Eric Nebling, Pinneberg (DE); Joerg Albers, Sankt Margarethen (DE); Gundula Piechotta, Hohenaspe (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 902 days.

(21) Appl. No.: 14/388,702

(22) PCT Filed: Mar. 27, 2013

(86) PCT No.: PCT/EP2013/056562
§ 371 (c)(1),
(2) Date: Sep. 26, 2014

(87) PCT Pub. No.: WO2013/144225
PCT Pub. Date: Oct. 3, 2013

(65) Prior Publication Data
US 2015/0060303 A1    Mar. 5, 2015

(30) Foreign Application Priority Data

Mar. 29, 2012 (DE) .................. 10 2012 205 171

(51) Int. Cl.
*G01N 27/28* (2006.01)
*B01L 3/00* (2006.01)

(52) U.S. Cl.
CPC .............. *G01N 27/28* (2013.01); *B01L 3/502* (2013.01); *B01L 3/502715* (2013.01);
(Continued)

(58) Field of Classification Search
None
See application file for complete search history.

(56) References Cited

U.S. PATENT DOCUMENTS

| 5,096,669 A | 3/1992 | Lauks et al. |
| 5,405,510 A | 4/1995 | Betts et al. |

(Continued)

FOREIGN PATENT DOCUMENTS

| EP | 1245285 A2 | 2/2002 |
| WO | 9805958 A1 | 2/1998 |

(Continued)

OTHER PUBLICATIONS

Schumacher et al., Lab Chip, 2012, 12 464.*

(Continued)

*Primary Examiner* — Eli S Mekhlin
(74) *Attorney, Agent, or Firm* — Duane Morris LLP (57) ABSTRACT

The invention relates to a measuring chip cartridge module conducting mobile multi-parameter analyzes of chemical and/or biological substances, comprising
a sample inlet for the extraneous introduction of a sample substance into said measuring chip cartridge module,
at least one separate reagent inlet for the extraneous introduction of reagents into said measuring chip cartridge module,
a measuring chip, the surface of which—designed for sample analysis—at least partially restricts an analysis (Continued)

cell with two openings, such that a liquid surrounding said sample substance can pass into the analysis cell through a first opening for the sample analysis, as well as a channel system, in which said sample substance can be conveyed from said sample inlet to said analysis cell and said reagents can be conveyed from at least the one reagent inlet to said analysis cell, wherein said channel system has no solid reagents, preferably no other substances apart from air and/or inert gas, prior to the introduction of said sample substance via said sample inlet and/or said reagents via at least the one reagent inlet. Furthermore, the invention relates to a system containing a replaceable cartridge module and likewise replaceable reagent storage and processing module, as well as a process for conducting sample analyzes in this system.

12 Claims, 9 Drawing Sheets

(52) U.S. Cl.
CPC ......... *B01L 3/527* (2013.01); *B01L 2200/027* (2013.01); *B01L 2200/028* (2013.01); *B01L 2200/04* (2013.01); *B01L 2200/148* (2013.01); *B01L 2200/16* (2013.01); *B01L 2300/0838* (2013.01); *B01L 2400/0406* (2013.01); *B01L 2400/0478* (2013.01)

(56) References Cited

U.S. PATENT DOCUMENTS

| | | | |
|---|---|---|---|
| 5,627,041 | A | 5/1997 | Shartle |
| 5,638,828 | A | 6/1997 | Lauks et al. |
| 6,374,684 | B1 | 4/2002 | Dority |
| 6,656,428 | B1 | 12/2003 | Clark et al. |
| 2001/0012612 | A1 | 8/2001 | Peterson et al. |
| 2002/0025576 | A1 | 2/2002 | Northrup et al. |
| 2002/0081233 | A1* | 6/2002 | Lappe ............... B01L 3/502 422/82.05 |
| 2003/0162304 | A1 | 8/2003 | Dority et al. |
| 2003/0170881 | A1 | 9/2003 | Davis et al. |
| 2004/0137607 | A1 | 7/2004 | Tanaami et al. |
| 2004/0189311 | A1 | 9/2004 | Glezer et al. |
| 2005/0054078 | A1 | 3/2005 | Miller et al. |
| 2005/0118061 | A1 | 6/2005 | Mototsu |
| 2006/0094028 | A1* | 5/2006 | Danna ............... B01L 3/502715 435/6.11 |
| 2007/0031283 | A1 | 2/2007 | Davis et al. |
| 2007/0111303 | A1* | 5/2007 | Inoue ............... B01L 3/0268 435/287.2 |
| 2007/0166192 | A1 | 7/2007 | Ehben et al. |
| 2007/0231213 | A1 | 10/2007 | Prabhu et al. |
| 2008/0014114 | A1 | 1/2008 | Van Atta et al. |
| 2009/0176314 | A1* | 7/2009 | Steinboeck ............ B01L 3/502 436/174 |
| 2010/0233824 | A1* | 9/2010 | Verhoeckx ........ B01L 3/502715 436/501 |
| 2010/0291588 | A1 | 11/2010 | McDevitt et al. |
| 2011/0301047 | A1 | 12/2011 | Immink et al. |
| 2012/0178091 | A1* | 7/2012 | Glezer ............... B01L 3/5027 435/6.12 |
| 2013/0011859 | A1* | 1/2013 | Putnam ............ B01L 3/502715 435/7.9 |

FOREIGN PATENT DOCUMENTS

| | | |
|---|---|---|
| WO | 2006042838 A1 | 4/2006 |
| WO | 2006125767 A1 | 11/2006 |
| WO | 2009062940 A1 | 5/2009 |
| WO | 2011063408 A1 | 5/2011 |

OTHER PUBLICATIONS

Highly-Integrated, Low-Cost In-Vitro Diagnostic Platform for Miniaturized Assay Development, Joerg Nestler et al., 14th International Conference on Miniaturized Systems for Chemistry and Life Sciences, 2010, p. 1223-1225.

Fully Integrated Lab-On-A-Disc for Simultaneous Analysis of Biochemistry and Immunoassay From Whole Blood, Beom Seolk Lee et al., Lab Chip, 2011, vol. 11, p. 70-78.

On-Chip Liquid Storage and Dispensing for Lab-On-A-Chip Applications, R. Boden et al., J. Micromech. Microeng., 2008, vol. 18, No. 075036.

Microfluidic Whole-Blood Immunoassays, Hai Jiang et al., Microfluid Nanofluid, 2010.

Automated Analytical Microarrays: A Critical Review, M. Seidel et al., Anal. Bioanal. Chem., 2008, vol. 391, p. 1521-1544.

\* cited by examiner

INTEGRATED DISPOSABLE CHIP CARTRIDGE SYSTEM FOR MOBILE MULTIPARAMETER ANALYSES OF CHEMICAL AND/OR BIOLOGICAL SUBSTANCES

The invention relates to a disposable measuring chip cartridge module (hereinafter also referred to in brief as "measuring chip cartridge module", "measuring chip cartridge" or "cartridge") for conducting preferably mobile multi-parameter analyses of chemical and/or biological substances, particularly for detecting and/or determining the concentration of target substances in liquid samples. Furthermore, the invention relates to a disposable chip cartridge system (hereinafter referred to in brief as "system"), having a replaceable measuring chip cartridge module, as well as a process for conducting analyses of this type in such a system.

Systems of this type are used in the area of mobile reproducible chemical and biochemical analyses, particularly in the area of point-of-care diagnostics. In this connection, the objective is pursued to forego a conventional inpatient laboratory analysis with unavoidable waiting times and instead to enable a method, with which the desired analysis results can be obtained directly and promptly (practically immediately) on-site, e.g. at the location of patient treatment.

The state of the art reveals the following systems, which are based on replaceable measuring cartridges for receiving and analyzing a sample:

WO 2006/125767 A1 reveals an analysis device for integrated and automated DNA or protein analysis, which is divided into a control device and a cartridge capable of being inserted therein in the form and size of a credit card. Said cartridge contains channel sections with various reagents in a dry and durable form, a sample port for pipetting a sample, PCR chamber for conducting a PCR (polymerase chain reaction), and a detection chamber with a DNA sensor. The water required for the analysis process is kept in said control device and supplied to the water ports of said cartridge inserted into said control device by means of fluidic components of said control device, including a pump and various fill level sensors. The control of the transport of water as well as the reading of measurement data occurs via electronics likewise housed in said control device.

US 2007/0166192 A1 presents a sample preparation module for receiving and preparing specific biological samples for an analysis in a standardized and miniaturized "lab-on-a-chip" cartridge. This module is designed respectively for a specific type of sample and has a cavity for complex or large-scale preparation steps, which cannot be conducted within said cartridge. These are, for example, the extraction and proliferation of cells of a target substance, mechanical homogenization of solid tissue samples, etc. The prepared sample is taken from said module through a suitably dimensioned and sealed opening directly to a sample inlet of said cartridge. Sampling and sample collection is conducted in said module either manually or through the use of gravity or by means of a movable piston in said cavity.

U.S. Pat. No. 5,096,669 reveals a system for conducting electrochemical measurements of bloods and other liquids with a disposable measuring unit, which can be inserted into a mobile reading device. Said measuring unit contains sensors, a pouch with calibration liquid, including mandrel, an air bubble reservoir, and a channel system with sample inlet. Said sample passes into said channel system through a capillary effect. The puncturing of said calibration pouch for measuring the calibration and conveying said sample to the sensor by compressing the air bubbles are triggered or controlled by said reading device.

U.S. Pat. No. 5,638,828 presents a sample device for collecting liquid samples and their introduction into a disposable measuring device for real-time analysis. Inside the sampling device, said sample is first collected in a reservoir, into which a precisely dimensioned capillary flows, which can be filled with said sample through the capillary effect. After manually connecting said sampling device with said filled capillary to said measuring device, both of its ends are connected to the inside of said measuring device. The sample liquid in the inside of said measuring device is moved around through targeted compression of an air bubble provided therein, which can move said sample along said capillary and further beyond said sensor.

US 2003/0170881 A1 reveals an apparatus for conducting various analyses on liquid samples. The adaptability to various analysis processes is ensured through "valve means" provided inside a disposable cartridge, such as constrictions, which impact the flow of said sample as well as a second calibration and rinsing liquid, including air bubbles, provided in a pouch in said cartridge. Said cartridge is inserted into a reading device, through which and from which pressure is exerted on certain paddle-shaped areas in the cartridge cover for conveying the fluids located in the cartridge. Calibration measurements are conducted prior to and after said sample measurement, wherein intermediate channels and sensors are cleaned with the second liquid. Reagents are provided in dry form in said channels of the cartridge.

U.S. Pat. No. 5,405,510 relates to a portable measuring unit for the measurement of multiple, sequential liquid samples. The apparatus has a disposable cartridge, which has access to an inlet to a flow-through cell with a hydrated sensor and, in contact with liquid, though spatially divided, with a reference electrode. In addition to the necessary electrical devices, said cartridge contains a flexible waste container. There is a check valve between said waste container and said flow-through cell. After calibration of said cell, a sample with an unknown quantity of a known analyte can be passed through the inlet.

In DE 102 45 845 A1, a measuring chip is revealed having a reaction area (analysis cell) capable of being overflowed by fluid, which enables a luminescence reaction and its measurement. Said measuring chip itself has spaces in addition to said analysis cell, which provide storage of sample liquid and reagents, are closed with a seal or a septum, and can be punctured with a syringe. However, it is not a closed unit in itself, but rather it interacts with a base plate, in which controllable fluid channels are arranged via valves, which can interconnect the storage spaces and said analysis cell.

Moreover, reference is made to the following documents: DE 10 1009 007230 A1 reveals a measuring cell with a flexible sidewall component, which ensures the sealing of a sensor chip and of a cover. We know from DE 41 39 121 C1 that the integration of the flow-through measuring cell in a measuring insert, which can be used in a basic device comprising the remaining components of the apparatus. US 2011/0301047 A1 suggests providing a detection apparatus with a valve between said inlet and said measuring chamber. EP 1 245 285 A2 reveals a sample inlet, to which a syringe can be applied. In WO 2009/062940 A1, a sensor cassette comprised of two permanently jointed, though separately manufactured modules and having a continuous measurement channel for receiving fluidic media; each module is connected electrically via a contact with an analyzer. The flow channels of an apparatus for the interchangeable reception of measuring cartridges or measuring cells pursuant to WO 98/05958 A1 have septa that can be repeatedly pierced; in addition, said apparatus has a sample receiver integrated in a valve block, which can be reached from outside for syringes or capillaries.

The familiar apparatuses and analysis methods require respectively one or more of the following measures:
  Batch-specific calibration through exemplary tests during/after production;
  Manual work steps during use, particularly during sample preparation;
  Special sample purification (particularly for optical detection methods);
and/or they are dealing with apparatuses characterized by one or more of the following components:
  Analysis devices having contained fluidic components (pumps, valves) for processing liquids in said device (i.e. liquid contact of device components) or alternatively, e.g. manual conveying of liquids as well;
  Consumables set having many various components and partially sophisticated use (pipettes, reagents, cartridges, chips . . . ).
Existing (point-of-care) systems, therefore, have some of the following disadvantages:
  No possibility of calibration during the runtime of the analysis;
  Significantly limited processing and control possibilities that are reduced to a minimum for said sample and reagents within said disposable measuring device, e.g. by means of a single air bubble for conveying as well as dividing the individual fluids;
  Necessity of using dry reagents and their dissolution/suspension in a channel or even micro-channel of said measuring cartridge during the actual analysis process with associated uncertainties with regard to their dispersion, concentration, and the overall timing;
  Inadequate quality of the reproducibility of analyses from test to test;
  Need for a manual sample preparation/dispensing prior to measurement, e.g. for blood samples;
  Contamination of analysis device components, particularly fluidic components, through contact with liquid, which requires extensive maintenance and care;
  Complicated, extensive logistics regarding consumables.
Overall, the need for a more automation or the increase of the degree of integration of complete biochemical analysis processes for mobile reproducible multi-parameter analyses, e.g. for the area of point-of-care diagnostics, must be retained.

Thus, the present invention is based on the task of providing an apparatus and a process for conducting preferably mobile chemical and/or biological sample analyses that enable an improved reproducibility of tests, better automation, and an increased degree of integration with the lowest possible costs and manufacturing and operating effort.

This problem is solved through a measuring chip cartridge module for conducting preferably mobile multi-parameter chemical and/or biological substances, comprising a sample inlet, through which a sample substance can extraneously pass into said measuring chip cartridge module, in addition to one or more reagent inlets, through which reagents can be extraneously supplied to said measuring chip cartridge module, e.g. from a suitable reagent storage and processing module, a measuring chip having surfaced designed for said sample analysis, which at least partially features a floor or a wall of an analysis cell with two openings, which is designed in such a manner that a liquid comprising said sample substance can be supplied to said analysis cell through a first opening, as well as a channel system, in which said sample substance can be conveyed from said sample inlet to said analysis cell and said reagents can be conveyed from at least the one reagent inlet to said analysis cell. The inside of said channel system does not contain any solid substances (reagents in solid form) required for the analysis prior to the start of the entire analysis process, and preferably no additional substances except for air and/or inert gas, which may pass into said analysis cell. Said measuring chip cartridge module pursuant to the invention may have particularly the design according to claim 1.

Said sample substance (in short: sample) can be supplied to said sample inlet in the form of a liquid, such as blood or serum, a solid or a swab sample.

A first reagent inlet externally separated from said sample inlet can be used, e.g. for the transport, dilution or liquefaction of said sample substance and/or for adding reactive substances necessary for the analysis. While said sample inlet itself can be tailored to the collection of said sample substance and normally closed following a completed sampling, this additional inlet into said cartridge allows further processing to be configured in a flexible manner.

The term "reagent" is used in this context in general for any substance that can pass into the channel system of said cartridge via a reagent inlet. Within the scope of the invention, e.g. chemically or biologically active substances, calibration solutions with known concentrations of one or more reference substances, buffer solutions, enzymatic solutions, substrate solutions, detector solutions, (e.g. isotonic) saline solutions, distilled water, cleaning solutions, air or inert gas may serve as reagents.

In one embodiment, said module pursuant to the invention comprises at least two reagent inlets, of which one can be used for supplying calibration solution to enable a calibration during runtime in a one-channel system, as described in further detail below. Naturally, there may be more than the two mentioned reagent inlets in this embodiment.

Within the context of the present application, in addition to a possible measurement of one or more parameters, such as the concentration of certain substances, e.g. of a chemical and/or biological nature, such as individual molecules, matter or cells (quantitative measurements), the term "measurement" and "measuring chip", etc. comprises their qualitative detection as well.

Said measuring chip may have, for example, electrodes potentially with receptor molecules for a target substance for conducting electrochemical analyses. Said electrodes can be designed as interdigital electrodes; the surface can be coated with gold or be comprised of gold for a simplified connection of receptor molecules via SH bonds. The measurement may be taken amperometrically, alternatively voltammetrically as well or with the help of both methods. An optical measurement for the sample analysis is also possible.

Said analysis cell is arranged on the surface of said measuring chip designed for the measurement, e.g. directly above a two-dimensionally designed measuring chip. In specific designs, e.g. a bottom of said measuring chip can be used for the measurement. Said measuring chip can also be arranged laterally within said cartridge, with a respective arrangement of said analysis cell on its interior surface designed for measuring with respect to said cartridge.

Said analysis cell (in short: cell) is designed for the reception of a liquid. It contains a first opening, through which said liquid can pass into said cell, while, e.g. air or used solution is forced out of said cell through said second opening.

A channel system is designed for transporting said sample and said reagents in said cartridge between the respective exterior inlets (meaning the sample and one or more reagent inlets) to said cell. It can contain interconnected as well as completely separated subsystems of channels within the cartridge.

Said channel system acts as, e.g. a connection of a reagent inlet with a said sample inlet within said cartridge to mix or prepare said sample prior to its entrance into said analysis cell with a reagent, as addressed briefly above.

Said cartridge pursuant to the invention does not contain any dry reagents in the channel system prior to extraneously adding reagents via the reagent inlets.

Preferred embodiments of the invention are provided in the dependent Claims and in the following description.

Said analysis cell preferably depicts a flow-through cell, i.e. a liquid can pass through said first opening into said flow-through cell and then partially or completely exit it through said second opening. By applying a vacuum pressure to the second opening, for example, via its connection to a reagent inlet, e.g. the flow or dispersion of the liquid to be analyzed can be influenced via the surface of said measuring chip.

Furthermore, a flow-through cell enables a successive analysis of a reference substance and a sample. Thus, for example, a calibration solution containing a known quantity of one or more reference substance(s) can be led through one of several reagent inlets into said flow-through cell and the contained reference substance(s), potentially qualitatively, semi-quantitatively or quantitatively determined after being linked to respective receptor molecules and/or with the help of additional reagents before said sample reaches the flow-through cell. In this manner, a calibration during runtime can be achieved with only one analysis cell via differential measurements, calibration curves, etc., as the analytes in the sample to be detected are qualitatively, semi-quantitatively or quantitatively compared with the reference substance(s) in the calibration solution.

However, one preferred embodiment of said cartridge has two identical analysis cells on the surface of the chip, such that the analysis of a sample in a first and a known reference substance in said second cell can be conducted simultaneously in order to calibrate/gauge said analysis process.

For the simultaneous and correlating processing of said sample and said reference substance between the respective outer inlet and the respective cell, two completely separate channel systems that are correlated for the purpose of identical processing are provided for in this embodiment. These channel systems can basically have different geometrical forms as it only depends on an objectively comparable processing in both channel systems, e.g. in terms of the course of time or quantity of applied reagents. This can be achieved, for example, (provided the samples and reference substance have approximately the same viscosity) through an approximately equal length of both channel systems.

In this embodiment, respectively two correlating reagent inlets connected to the respective channel system are provided, one of which serves to supply said reference substance and the other of which serves to supply air, a buffer solution, enzymatic solution, substrate solution or similar, as describe above for the one-piece system.

Preferably two or more reagent inlets are designed in said cartridge, through which two or more various reagents can be supplied to a channel system. The reagent inlets connected to the various channel systems can be, e.g. arranged as two parallel rows in combination with the above preferred embodiment.

Due to the extraneously accessible arrangement, respectively two different reagent inlets can be independently operated in the cartridge pursuant to the invention, e.g. filled with liquid reagents or impinged with negative or positive pressure. As a result of their basically similar design, the different reagent inlets can also be operated similarly, e.g. synchronously.

With the increasing number of reagent inlets, the flexibility, adaptability to the demand of an application, as well as, if desired, the complexity of the multi-parameter analyses to be conducted with said cartridge increases both with respect to the selection of reagents as well as with respect to the analysis process.

In a cartridge pursuant to the invention, a rinsing channel for moving the sample collected in the sample inlet can be provided for in the channel system. Said rinsing channel can, for example, in the channel system, flow into said sample inlet, potentially with a constriction or capillary stop at the point of outlet, such that rinsing said sample can only occur if pressure is applied to the rinsing channel. The other side of said rinsing channel ends in any event in a reagent inlet for supplying a rinsing fluid, e.g. a buffer solution or air.

In specific designs with a rinsing channel, e.g. swab samples, can be removed by means of a filter pad, carried into the sample inlet (e.g. in the form of a pressed circle), and then flushed through or into said channel system. In this context, e.g. a syringe module attachment can be used. Said sample can be flushed out or through said filter pad into said cartridge by means of syringe module filled, for example, with a rinsing solution (e.g. a buffer).

Said sample can be taken for liquid samples, e.g. for whole blood, through one or more capillaries integrated in said sample inlet. Due to the capillary effect, a capillary having given dimensions is filled, for example, by applying a sample droplet, through which a sample is automatically dispensed. After closing the sample inlet with a cap, the sample volume dispensed in this manner can be processed in said cartridge, e.g. in an automated process.

In a further embodiment, which likewise comprises a rinsing channel, a cap channel is situated in said cap, which provides a liquid-tight connection between said capillary inlet and said rinsing channel when said sample substance inlet is closed. Said sample can be extruded from the sample capillary into the channel system for further processing and potentially simultaneously pre-diluted through air or a liquid from said rinsing channel. In a simple case, said cap channel has the form of a u-shaped pipe.

In a channel system pursuant to the invention, a pre-diluted sample or even one that has not been pre-diluted can subsequently be conveyed from said sample inlet directly to a first dilution and/or waste chamber for potentially further dilution. In this regard, this chamber can be connected to a reagent inlet for supplying liquid/air, wherein dilution or rinsing liquid can be supplied to said chamber, e.g. via a rinsing channel. Alternatively or additionally, said chamber can be connected to a reagent inlet, in which said diluted sample can be absorbed for the purpose of further processing. Furthermore, said chamber can alternatively or additionally be connected to the second opening of a flow-through cell for receiving said analyzed sample.

Preferably at least one mixing chamber (in short: mixer) is provided in the one or in each channel system pursuant to the invention, in which said sample or a reference substance can be mixed with one or more reagents on the way to the analysis cell. The respective mixer in this case is connected to one or more reagent inlets. A buffer, a substrate, an enzyme, and/or a detector can be added, e.g. to a potentially pre-diluted sample in a mixer. These steps can also be divided among various mixers and, e.g. occur successively.

Said measuring chip preferably has and electrical connection point, to which an external device for reading measurement data can be connected. Said electrical connection point (connection) can be arranged, e.g. on a side opposite the surface of said measuring chip designed for the sample analysis, through which the electrical connection can be prevented from coming into contact with liquid. This can be achieved by means of electrical vias through said chip to its bottom side. In the process, the electrical structures necessary for electrical data processing can be arranged directly in the measuring chip (e.g. in the form of an application-specific integrated circuit [ASIC]) or achieved in the external device. An ASIC can also be provided in said cartridge on a substrate separate from said measuring chip. Said chip can, for example, be arranged on said cartridge such that it is impervious to liquids through lateral press fitting by means of an elastic, liquid-tight material, such as silicon or polydimethylsiloxane (PDMS).

The sample can be taken in a simple case directly by means of said sample inlet. However, additional agents for collecting said sample substance can be situated in a separate sampling module in said cartridge pursuant to the invention. Said sampling module comprises a sample outlet, which can be connected to the sample inlet of said cartridge in a liquid-tight manner for the purpose of transferring the sample (e.g. using capillary forces) to the channel system. In this case, said sample can be taken prior to or after interlocking the sampling module with the sample inlet. Said sampling module is preferably likewise an inexpensive disposable item, for example, in the form of a plastic or glass capillary with a tube end piece having a tear-open membrane for connecting to the sample inlet on one end and to a cap on the other end. One benefit of a separate sampling module consists, e.g. in the possibility of only replacing it and not the entire measuring chip cartridge, for example, in the case of failed sampling.

In specific designs of the cartridge pursuant to the invention, there are no further substances other than air and/or protective gas, e.g. inert gas, in said channel system prior to introducing said sample substance via the sample inlet and/or a reference substance via a reagent inlet. If necessary, water, particularly distilled water, can additionally be provided in the channel of said cartridge in advance.

Another aspect of the invention is a modularly structured disposable measuring chip cartridge system (in short: system) consisting of two separable main modules capable of being interlocked: a disposable cartridge pursuant to the invention and a disposable or reusable reagent module with one or more reagent cylinders for receiving reagents, wherein each cylinder has a cylinder outlet for a liquid-tight connection to a reagent inlet of said cartridge as well as a moveable piston (drive piston) for conveying said sample and said reagents in the system. The system pursuant to the invention is specified in Claim 12.

The storage and addition of reagents as well as mechanical means for moving all gasses and liquids in the system (i.e. primarily in said cartridge) are situated in a separate module—the reagent module—in the system pursuant to the invention. In general, the use of pasty masses or powder-like substances in said reagent module is likewise not precluded.

The system can be connected to an external control and reading device (so-called control unit) having a processor and at least one electromechanical actuator for actuating the pistons. Said control unit can preferably be connected to the measuring chip via a purely electrical interface and to said reagent module via a purely mechanical interface. In this way, it does not come into contact with the liquids involved in the analysis when the system is properly operated and, therefore, does not have to be cleaned from these liquids or maintained for this reason alone.

The reagent module pursuant to the invention has already been prepared with one or various reagents in liquid form, i.e. prior to the actual analysis process, and is delivered, e.g. in a condition ready for use, by the manufacturer or filled on-site by chemically/technically trained personnel. In addition to chemically and/or biologically active substances, the term "reagents" in this context also includes water, particularly distilled water, air or other fluids that can be used in an analysis process.

The use of reagent cylinders having pistons in a uniform block enables on the one hand a simple, robust, and reliable mechanical actuation of the entire fluidics, i.e. all gas and liquids movements in the channel system of said cartridge. On the other hand, it enables any high degree of integration of all fluidic processes in the system, e.g. through a synchronous or conveniently mutually coordinated actuation of various pistons.

When this system is put together, said pistons can on the one hand supply reagents to the cartridge and move them further therein by generating pressure. On the other hand, said pistons can also provide suction or move substances back and forth, i.e. act as pumps, by generating negative pressure.

The actuation of said pistons pursuant to the invention is in principle similar for all pistons and may occur at a shared location, namely on a mechanical interface between said reagent module and said control unit. The actuation of two or more pistons can, for example, originate from a shared electromechanical actuator, e.g. a motor, or from multiple identical actuators in said control unit. Said control unit can have, e.g. for its part an equal number of pressure and/or suction pistons, for actuating said drive pistons. They can apply pressure to the drive pistons, for example directly or pneumatically, or by suitable means of fastening or again pneumatically pull on said drive piston, namely respectively on one of the cylinder ends opposite the cylinder outlet.

As a result of the basic possibility as well as an independent as well as conveniently coordinated actuation of the different drive pistons in said reagent module, the system pursuant to the invention ensures practically unlimited flexibility of a multi-parameter analysis as well as with respect to the number and selection of said reagents as well as with respect to the temporal process of an analysis process without any loss with regard to structural complexity or costs.

Moreover, said reagent module pursuant to the invention generally enables a visual inspection of its functionality and integrity, e.g. with the use of transparent or at least translucent glass or plastic cylinders or this type of reagent block. Thus, at least gross errors, such as the clogging of one of the fluidic channels in the system, can be determined immediately. This is a benefit compared to the extraneously invisibly running analyses within miniaturized cartridges with dry reagents that are concealed in the reading device, such as those revealed by the state of the art.

With the system pursuant to the invention, modifying or adding analysis steps, potentially with the addition of other/ further reagents, is extremely easy to do as a result of the depicted modular design of the system and the possibility of flexible digital control by means of a purely electromechanical control unit, as it basically does not require any structural changes in the design of the measuring cartridge. Other reagents can be used simply by making a modification to the control software and potentially by acquiring a (disposable) reagent module; however, manufacturing costs or reproducibility of analyses will not be impacted in doing so.

Furthermore, the structural principle of the system pursuant to the invention does not in principle become more sophisticated or extensive even with an increasing number of reagent cylinders in the reagent module and/or the channel systems in the cartridge. That is, the manufacturer can offer multiple variations of the measuring chip cartridge and reagent modules with a different number or arrangement of reagent cylinders or channel systems without converting to other manufacturing technologies.

Due to the possibility of a complete automation of the entire analysis process starting with completed sampling and the homogenous, centralized actuation of all analysis processes, the system pursuant to the invention ensures maximum reproducibility of the analysis from measurement to measurement.

The invention enables an integration and automation of reagent storage, sampling, sample dilution, reagent processing, detection as well as calibration and control functions in a disposable cartridge system for mobile multi-parameter analyses.

In a preferred embodiment, the system has a cartridge as described above with two identical analysis cells for the parallel measurement of a sample and a reference substance as well as a reagent module having two correlating reagent cylinder sets, which enable equal processing of said sample and said reference substance. Preferably, it involves two identical sets of reagent cylinders, which can be arranged, e.g. parallel to each other in said reagent block.

In any event, one or more cylinder outlets are closed prior to being joined with said cartridge, preferably by a membrane, wherein the respective reagent inlet or inlets of said cartridge can respectively have a hollow needle, e.g. a tube, for puncturing said membrane. Preferably, all cylinder outlets are respectively closed with this type of membrane prior to being joined with said cartridge, e.g. by a membrane shared for one cylinder bank.

The replaceable modules pursuant to the invention can be manufactured in a cost efficient manner, e.g. from plastic through injection molding.

The modular system pursuant to the invention includes the following benefits:
A high level of reliability through integrated calibration and control functions;
A high degree of reproducibility of said analyses through automated processing in the integrated measuring chip cartridge;
Simple operation (minimal sources of operating errors);
A robust system, particularly well-suited for mobile use;
(Cost) efficient logistics of consumables due to simple manufacturing, storage, transport of said consumables.

The inventions is also based on a process for conducting multi-parameter analyses of chemical and/or biological sample substances by means of a system pursuant to the invention, for which:
a) said sample substance at the sample inlet is admitted into a sample receptacle, preferably a capillary, of an unused measuring chip cartridge module,
b) said measuring chip cartridge module is joined with said reagent module in a liquid-tight manner,
c) the analysis of said sample substance is conducted, wherein said sample substance and said reagents in the system are conveyed by means of said drive pistons,
d) the used measuring chip cartridge module is replaced with an unused measuring chip cartridge module prior to each new sample measurement.

Individual characteristics or characteristic combinations, etc. of an operating process pursuant to the invention, potentially specifically for one embodiment, can be found in the above description of said measuring chip cartridge module and the system pursuant to the invention as well as the description of the design examples based on the figures following further below.

In addition to point-of-care diagnostics (e.g. for immunology assays) and other medical areas (e.g. for multi-parameter bioanalyses based on protein tests for mobile use), said system and the process pursuant to the invention can be applied wherever a rapid, mobile, and cost-effective electrochemical analysis of samples is needed.

Preferably, not only the disposable cartridge, but also the reagent module is replaced with an unused one prior to every sample measurement. However, this is not absolutely necessary. In fact, a reagent module can be used for two or more sample measurements and separated from the removable cartridge in a liquid-tight manner between measurements, e.g. via the pistons.

A calibration or control functions can be actualized during runtime with the system pursuant to the invention, by using two analysis cell on one chip (or 2 analysis arrays) for separate, simultaneous processing of an actual sample and a calibration solution (e.g. a defined analyte solution). A simultaneous, and with respect to the timing and addition of a reagent, equal (and as identical as possible) processing of said sample and reference substance can be actualized, e.g. through synchronous actuation of the pistons in the correlating (e.g. identical) reagent cylinders designed for the sample and reference substance.

Figure 5:
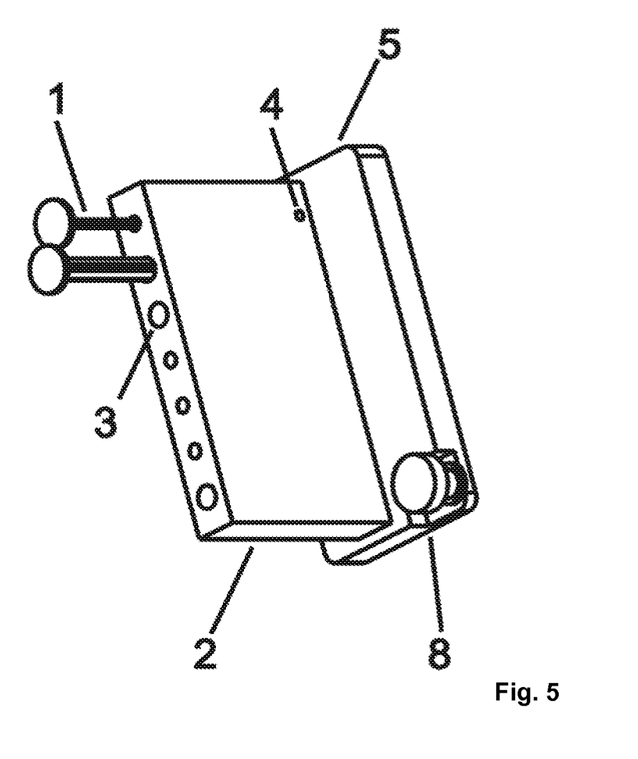
FIG. 5 a second design example of the system pursuant to the invention having a single measurement channel.
Figure 6:
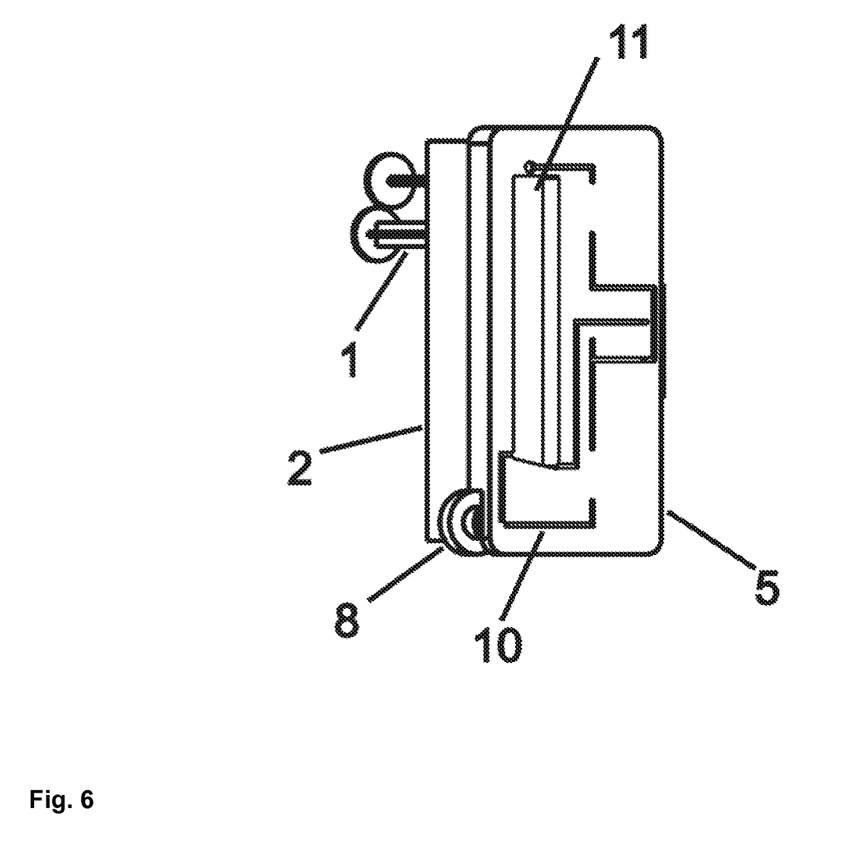
FIG. 6 a perspective depiction of the example from FIG. 5 (view from below)
Figure 7:
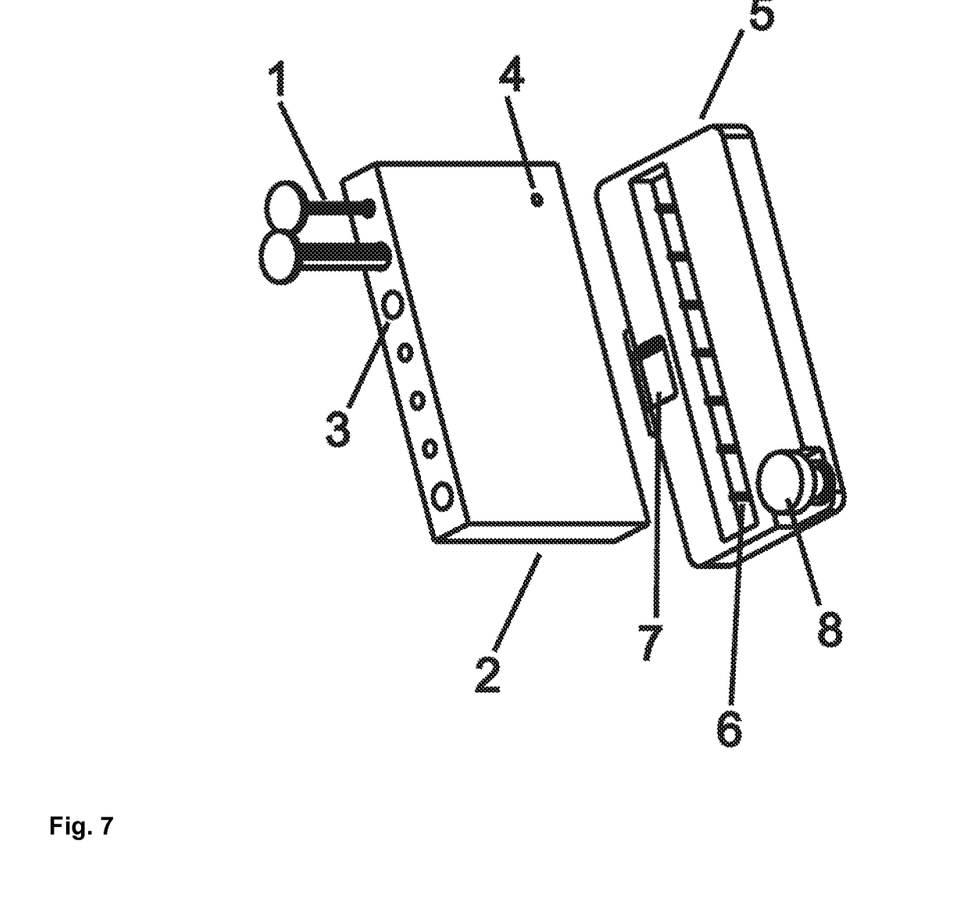
FIG. 7 a perspective exploded view of the example from FIG. 5 (view from above)

Said calibration solution can be also be integrated in a sample buffer, e.g. with an alternative embodiment of said cartridge with only one analysis cell (see FIGS. 5-7). Calibration positions can be provided in said analysis cell, which preferably represents a flow-through cell, for calibrating with such a variation. With such a design, a calibration can be performed during runtime, as explained above.

Controlling the transport of liquid via the chip is possible, for example, by measuring the heat output in conjunction with a chip temperature control. In this regard, e.g. changes to the chip temperature (regulated to specific target values) are monitored via cooling effects when pumping air instead of liquid across the chip. This can serve to detect defective functioning of the pumps (or the pistons or their actuator) or leaks in the cartridge.

The analysis pursuant to the invention can be controlled by an external device—a control unit. Its connections to the system pursuant to the invention are preferably designed in such a manner that said control unit does not come into direct contact with the liquids, which flow during the analysis in the system. In this regard, said control unit can be connected, e.g. purely electrically to said measuring chip cartridge module and purely mechanically to said reagent module. Said analysis process can be run fully automatically in the composite system controlled by said control unit, wherein said sample substance and said reagents (and/or potentially said reference substance) are transported in the system via the actuated drive pistons.

Contamination of a controlling device known for conventional systems by liquids involved in the analysis can be precluded with the system pursuant to the invention through a complete separation of interfaces to the control unit, in which there is

- a fluidic interface only between said cartridge module and said reagent module (as well as within said cartridge module to the integrated chip and potentially to said sampling),
- an exclusively mechanical interface to said control unit for the operation of fluidics in the system via said reagent module, and
- an exclusively electrical interface to said control unit for contacting the electrical array measuring chip,
- as well as potentially a thermal interface to an additional temperature module if there is no "on-chip temperature control", when operating the system.

Only one combination of reagent module (storage of liquid reagents) and chip cartridge module (sampling and dilution function plus measurement) is necessary as a consumable material for the operation of a system pursuant to the invention. However, in contrast to conventional systems, the potentially existing control unit does not have to be specially maintained, filled, cleaned or replaced.

The removal and disposal of said modules is possible in the form of a closed liquid-tight unit, such that there is no threat of contamination and injury to the user or the patients.

During the installation and contacting of said chip, reducing the spatial requirement on said chip (with an associated cost reduction) is possible for electrical contact and fluidic sealing. While both are typically situated on the top of the chip in familiar systems, the following are optionally possible as well in the system pursuant to the invention in addition to the likewise possible contacting of the top of the chip:

electrical vias to the bottom of the chip
(optionally a 3-D design as well: ASIC+Bio-MST) and/or chip installation including fluidic sealing potentially by means of lateral press fitting via an elastic, liquid-tight material (e.g. silicon, PDMS).

The specific examples of individual fluidic functions in a system pursuant to the invention depicted above and in the following, such as the calibration method, sampling, sample dilution, reagent storage and processing should not be considered to be final. The system and operation procedures pursuant to the invention also allow for other combinations of individual fluidic processes and their application-specific variations other than those explicitly depicted, which are readily apparent for specialists.

Additional benefits of the invention are exemplified in the following based on the design examples depicted in the drawings and the associated description. They should not have any restrictive effect for the object of the invention, but rather serve as specific examples for it. Particularly, the figures are schematic diagrams, which are not true to scale.

The following are presented.

Within the scope of the invention, a biochip of the type described in DE 10 2008 027 038 A1 can be used as a measuring chip for said sample analysis. Thus, the following description of the specific embodiments presented in the figures relates in a purely exemplary manner to such a biochip as a measuring chip in the context of the invention. Other types of measuring chips, particularly those for purely chemical analyses, can be used in all cases.

LIST OF REFERENCE NUMBERS

Figure 1:
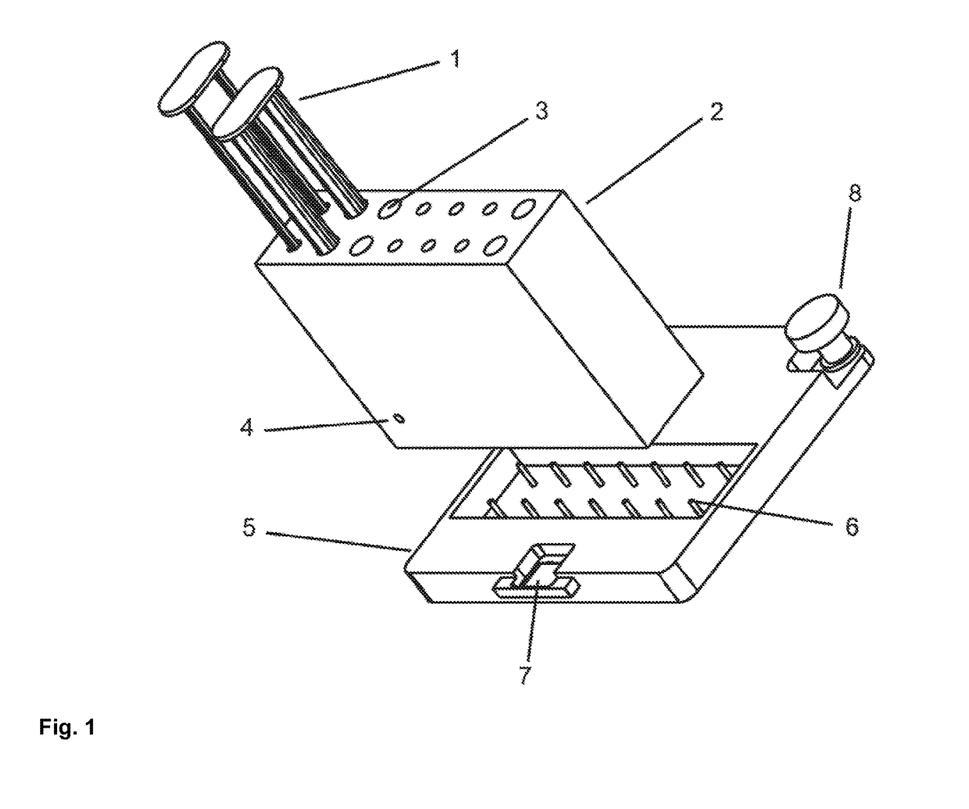
FIG. 1 a first design example of the system pursuant to the invention having two parallel measurement channels for a calibration during the runtime of said sample analysis.

1 Piston
2 Reagent block
3 Reagent cylinder
4 Ventilation hole
5 Cartridge
6 Connector pin
7 Biochip
8 Cap
9 Membrane
10 Fluidic channels
11 Dilution/waste chamber
12 Sealing foil
13 Sample inlet
14*a* Flow-through cell A
14*b* Flow-through cell B
15 Piston actuators
16 Calibration inlet FIG. 1 presents a perspective depiction of a first design example of the system pursuant to the invention having two correlating measurement channels, which enable a calibration of said sample analysis during runtime. The depicted integrated biochip cartridge system contains two replaceable main modules, a reagent storage and processing module (in short: reagent module) 1-4, and a biochip cartridge module (in general: measuring chip cartridge module; in short: cartridge) 5-8.

Figure 2:
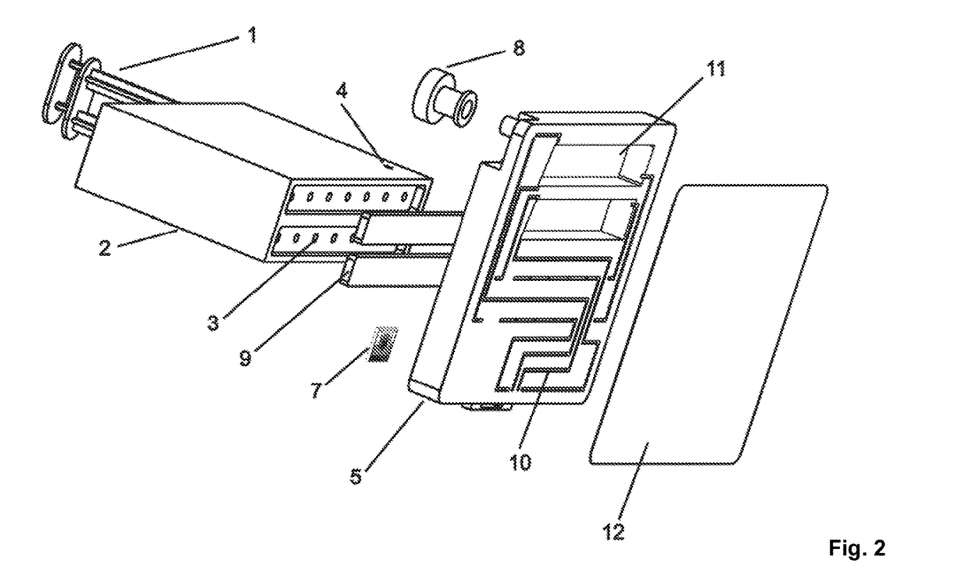
FIG. 2 a perspective exploded view of the example from FIG. 1 (view from below)
Figure 3:
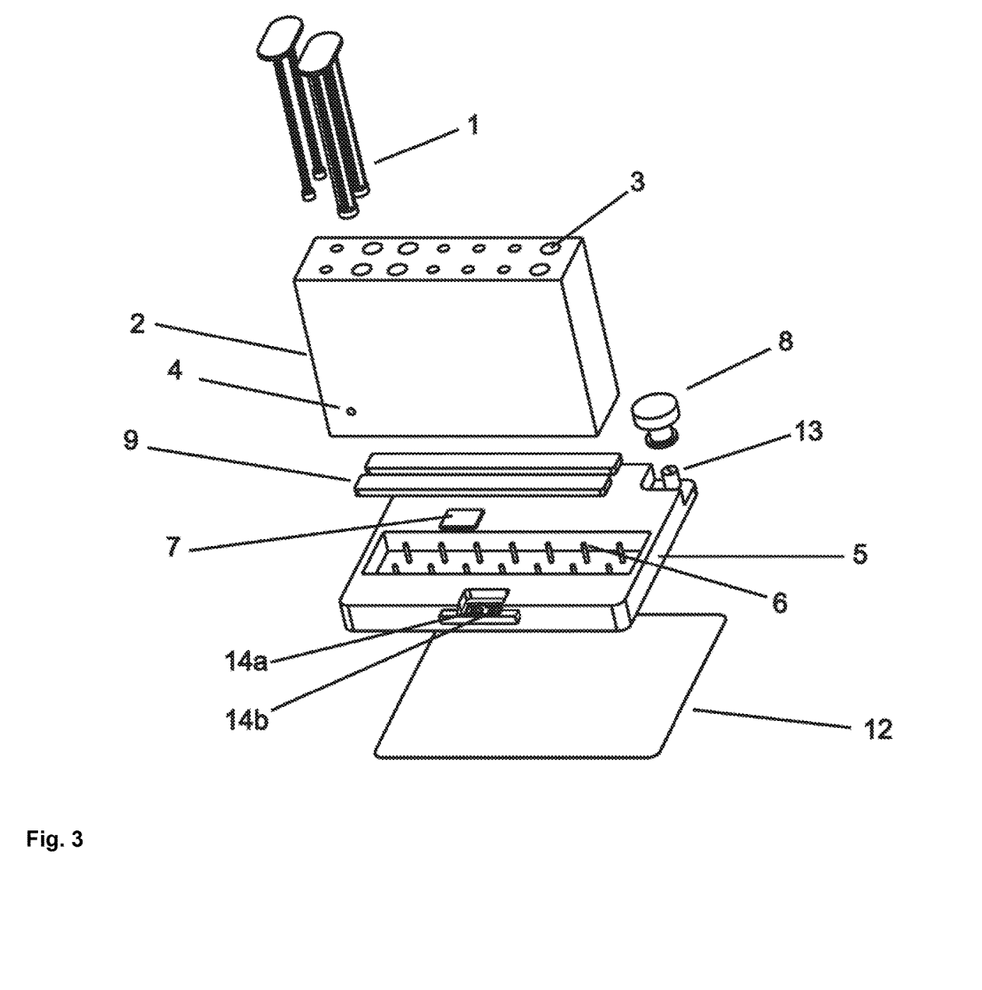
FIG. 3 a perspective exploded view of the example from FIG. 1 (view from above)

The individual components are presented in detail in the exploded view in FIG. 2 (from below) and in FIG. 3 (from above).

The various reagents required for said analysis are stored in reagent cylinders 3 of reagent block 2. Said reagent cylinders are sealed by drive pistons (in short: pistons) 1 and membranes 9.

Biochip 7 in an array format (e.g. with interdigital electrodes) represent a detection unit for multi-parameter analyses. It is integrated into measuring chip cartridge (in short: cartridge) 5 and connected to the one, or in this example, the two separated and correlating channel systems (hereinafter also: fluidic systems), i.e. fluidic channels 10 and dilution/waste chamber 11 for the sample measurement channel (or the respective dilution/waste chamber for said calibration measurement channel). A sealing foil 12 is used to seal said fluidic channels and said dilution/waste chambers.

For easy sampling with a defined volume, there are one or more sample capillaries having given dimensions in sample inlet 13, which is closed after sampling with cap 8. Said sample inlet is particularly suited for receiving droplets, such as capillary blood from a fingertip. If said sample substance was collected or prepared in a separate reservoir, e.g. a syringe, it can be supplied to said sample inlet likewise in the form of droplets through of a tube. Said liquid sample substance subsequently fills said sample capillary/capillaries due to the capillary effect.

Figure 8:
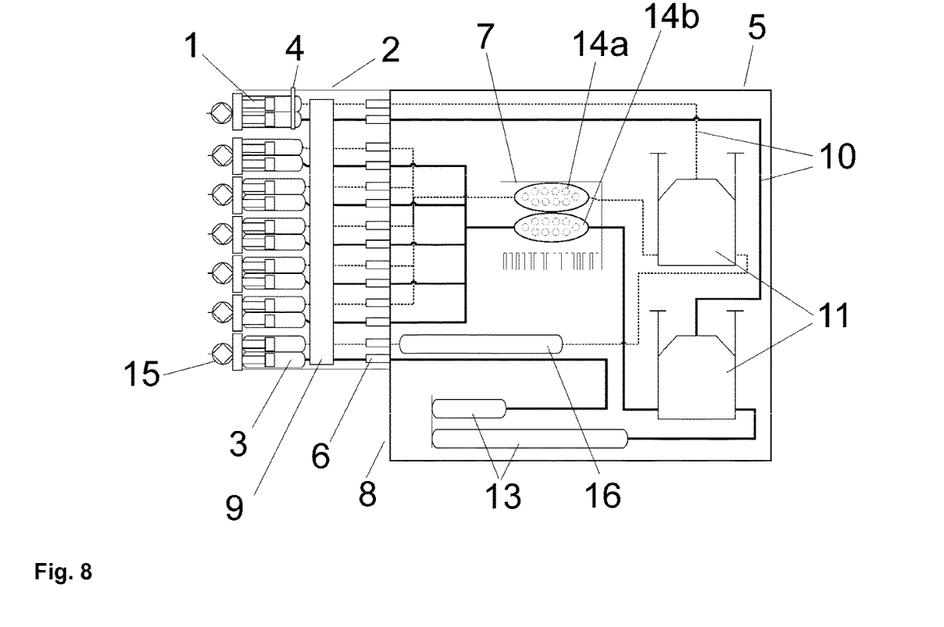
FIG. 8 a schematic depiction of the individual fluidic functions in the system according to a first design example.
Figure 9:
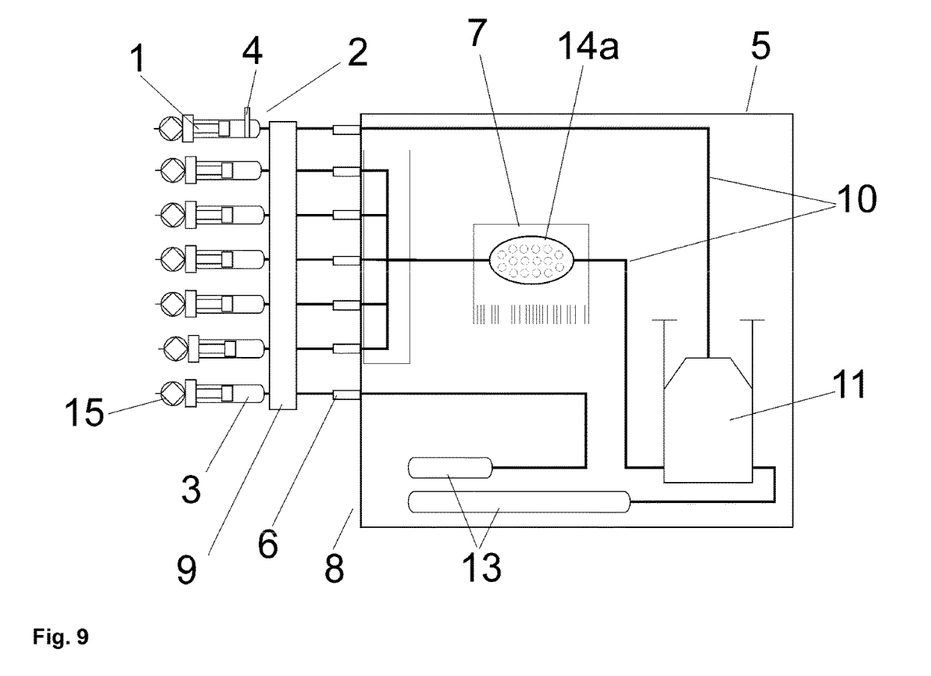
FIG. 9 a schematic depiction of the individual fluidic functions in the system pursuant to the invention according to a second design example.

Said collected sample substance from the sample capillary is introduced into said fluidic system of said cartridge, for example, through extrusion of said sample substance by means of air or a rinsing liquid, which is supplied to said sample capillary/capillaries via a channel within said cap when said sample inlet is closed—see also the diagram in FIG. 8/9. Alternatively, said sample substance can be absorbed from said sample capillary into said fluidic system of said cartridge as well by producing a vacuum at said capillary outlet by means of a suitable piston in a connected reagent module.

When joining said cartridge module with said reagent module, connector needles or tubes 6 make a fluidic connection of said modules by puncturing membranes 9. The solutions for the implementation of the fluidic processes during said analysis process are processed via pistons 1, which convey the respective reagents from reagent cylinders 3 into the cartridge. Thus, ventilation holes 4 are opened, i.e. during said fluidic processing. In the process, said pistons generally independently moved in a special device/said control unit (not shown) with the help of automated mechanical drives. In addition to the drive functions for fluidic control, said device also performs the reading functions for said biochip.

Said control unit may comprise, for example, an electromechanical drive for pistons 1, a processor for the digital evaluation of the measurement signals from said biochip and for controlling said measurement processes, and a reading device for reading measurement protocol software. Said control unit, particularly its electrical connections to said cartridge 5 and mechanical connections to said reagent module, is not placed in direct contact with the liquids processed in said system or those to be processed. As a result, the maintenance and cleaning measures required with familiar devices are omitted for said control unit, and cartridge 5 and reagent block 2 can simply be replaced after each measurement.

After plugging reagent block 2 into cartridge 5, connecting to said control unit, and closing said sample inlet with said cap, the analysis process can run fully automatically—controlled by said control unit.

Figure 4:
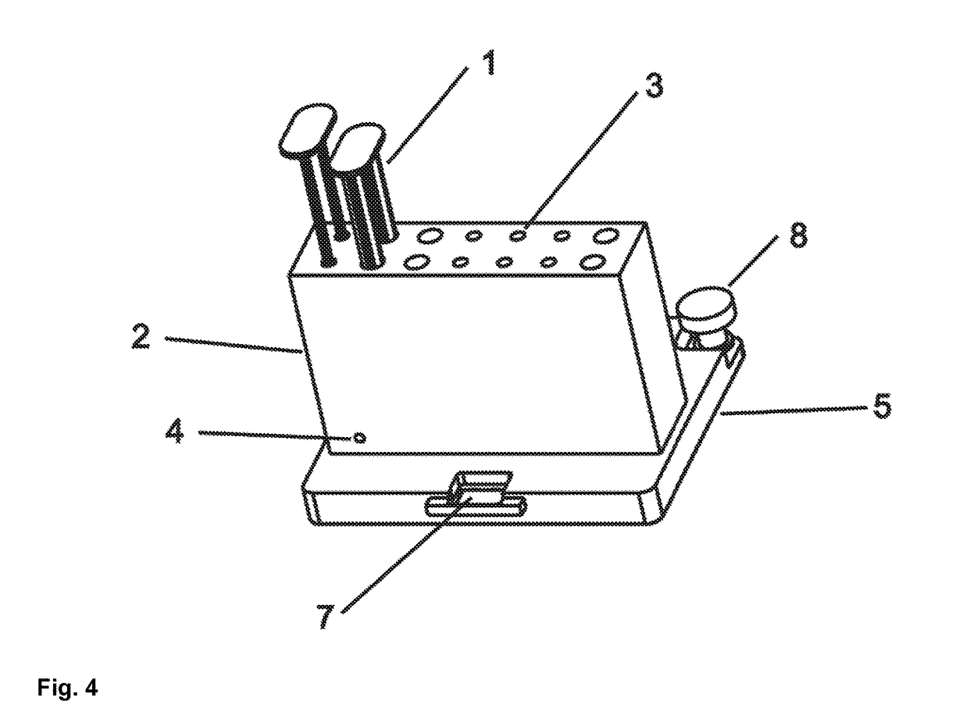
FIG. 4 main modules from FIGS. 1-3 in a conflated state.

At the end of said analysis process, cylinders 3 can be can be closed with ventilation holes 4 through the respective pistons from cartridge 5. Subsequently, said cartridge module can be removed and disposed of as a closed unit, while said reagent module can be used for another measurement. Alternatively, both replaceable main modules can be disposed of after the measurement as a joined and likewise closed unit that is outwardly impervious to liquid (FIG. 4).

FIG. 1-FIG. 4 present the first embodiment according to the invention with a 2-measurement channel calibration functionality, i.e. there are two separated fluidic systems, which can be synchronously operated via a coupling in the drive system, e.g. through a mechanical connection of said pistons.

FIG. 8 outlines the respective individual, particularly the fluidic functionalities, in a schematic diagram. Said sample is first supplied in a fluidic system of cartridge 5 via sample inlet 13. Controlled via pistons 11, said sample is then diluted and mixed with a sample buffer in a first dilution/waste chamber 11. In a second fluidic system, a calibration solution with known analyte concentrations is simultaneously rinsed in a second dilution/waste chamber, which can be seen in the perspective depiction of FIG. 2 below chamber 11.

The respective solutions are moved from the dilution/waste chambers by means of pistons 1 pursuant to the type of syringe pump drives P1-P6 in the respective fluidic system (or channel system) of cartridge 5 for processing said sample and calibration solution through flow-through cells 14*a/b* via said biochip. In this process, said liquids can also be suctioned in the cylinders of said reagent module in the case of specific analysis processes.

Subsequently, a backwashing occurs into said dilution/waste chamber. These processes run synchronously for both fluidic systems, just as the rinsing of additional reagents via said biochip into the waste chamber. In the process, the various areas on said biochip, which are separated through both separated flow areas, undergo an identical process. In connection with the precise knowledge about the composition and/or parameters, such as concentrations, the reference substance/calibration solution, in this manner, a precise calibration of said sample analysis can be made during runtime. Furthermore, additional functions, such as positive control positions in each flow area and the control of the flow of liquid via said biochip, lead to an improvement of quality control with each analysis.

FIG. 5-FIG. 7 as well as FIG. 9 represent a solution pursuant to the invention without a 2-measurement channel calibration function. Said calibration can be made in such a system via individual calibration positions on the same array in a shared flow-through cell of said measuring chip, as described above.

The degree of integration of the analysis processes in the system pursuant to the invention are increased significantly compared to conventional systems through similar, potentially shared, potentially even identical and/or simultaneous control of pistons 1 for conveying reagent and sample substance to fluid channels 10 (in the process, actuation occurs potentially simultaneously and identically for said samples and potentially the reference measurement channel) and said sample inlet closed by said cap.

The sample volume can be dispensed, for example, by a precise measurement of said sample capillary, which is completely filled with said sample through capillary forces upon submersion into the sample liquid (e.g. into a droplet). When using swab samples on filter paper with a known absorbency, said sample substance can be dispensed, e.g. by pressing out the given volume of swab sample and adding a precisely measured volume of rinsing liquid. In the case of solid, powder-like sample substances, such as dry blood, precise dispensing may occur by filling a container (e.g. integrated in said sample inlet) with a given volume and by adding a given volume of solution or rinsing liquid. Through a fully automated addition of various reagents from said reagent module to said cartridge, manual dispensing by the system operator is insubstantially reduced or, at best, reduced to a reproducible minimal activity, such as filling a visible container with dry powder.

What is claimed is:

1. Disposable chip cartridge system for conducting mobile multi-parameter analyses of chemical and/or biological substances, comprising:
   a) a replaceable measuring chip cartridge module, comprising
      sample inlets for the introduction of a sample substance into the measuring chip cartridge module,
      at least one separate reagent inlet for the introduction of reagents into said measuring chip cartridge module, a measuring chip, the surface of which at least partially confines two analysis cells each with two openings, such that a liquid comprising said sample substance can pass into the analysis cells through a first opening for sample analysis, as well as two separate channel systems, in which said sample substance can be conveyed from said sample inlets to said analysis cells and said reagents can be conveyed from the at least one reagent inlet to said analysis cells, wherein said channel systems do not comprise solid reagents, and no other substances apart from air and/or inert gas, prior to the introduction of said sample substance via said sample inlets and/or said reagents via at least the one reagent inlet;

as well as b) a replaceable reagent module designed as a uniform block, having two or more reagent cylinders for receiving reagents, wherein each cylinder is designed with a drive system including a drive piston for conveying said sample substance as well as said reagents in the system and a cylinder outlet for the liquid-tight connection to a reagent inlet of the measuring chip cartridge module, wherein the cylinder outlets of the replaceable reagent module are closed by a membrane, and the respective reagent inlet or inlets of said measuring chip cartridge module include a hollow needle for puncturing said membrane, wherein said two identical analysis cells on said surface of said measuring chip designed for the analysis of samples correspond to said two separate channel systems, for simultaneously processing the sample substance and reference substance for the calibration of the sample analysis, and wherein said two separate channel systems are configured to be connected to two different reagent cylinders via the respective hollow needle and wherein the respective drive systems of said two different reagent cylinders include a coupling designed for synchronously operating the two drive systems.

2. System according to claim 1, in which said analysis cells of said measuring chip cartridge module are flow-through cells, such that a liquid comprising said sample substance can pass into said flow-through cells through the first opening and exit said flow-through cells through a second opening.

3. System according to claim 1, wherein two reagent inlets corresponding to each other are provided, one of which is provided for introducing air or buffer to dilute samples and the other is provided for introducing a reference substance.

4. System according to claim 1, in which said measuring chip cartridge module has two or more reagent inlets for the introduction of two or more different reagents into the channel systems.

5. System according to claim 1, in which said channel systems of said measuring chip cartridge module have a rinsing channel for rinsing said sample substance from said sample inlets for conveying to said analysis cells, wherein one end of said rinsing channel is a reagent inlet for receiving a rinsing fluid.

6. System according to claim 1, in which said channel systems of said measuring chip cartridge module have a first dilution and/or waste chamber, which is connected to the said sample inlets for receiving said sample substance and/or to an inlet for ventilating and/or to a reagent inlet for the further conveying of said sample substance to said analysis cells and/or to a second opening of flow-through cells for receiving a used sample substance, in which a liquid comprising said sample substance can pass into said flow-through cells through the first opening and exit said flow-through cells through the second opening.

7. System according to claim 1, in which said channel systems of said measuring chip cartridge module have one or more mixing chambers, in which said sample substance or a reference substance can be mixed with one or more reagents along the way to said analysis cells, and which are connected for this purpose to said sample inlets and/or one or more reagent inlets.

8. System according to claim 1, in which said measuring chip of said measuring chip cartridge module has an electrical connection for connecting to an external device for reading the measurement data.

9. System according to claim 1, comprising a detachable sampling module for collecting said sample substance with a sample outlet, which can be attached to said sample inlets of said measuring chip cartridge module in a liquid-tight manner.

10. System according to claim 1, further comprising a replaceable reagent module having two identical sets of reagent cylinders.

11. System according to claim 1, in which said sample inlets of said measuring chip cartridge module have a capillary for receiving said sample substance as well as an end cap for closing said capillary after taking a sample.

12. System according to claim 11, in which said end cap has an end cap channel that, during a closed condition of the sample inlets, is linked to the capillary in a liquid-tight manner, in order to connect the capillary to said rinsing channel.

* * * * *